United States Patent
Kang

(10) Patent No.: US 8,084,639 B2
(45) Date of Patent: Dec. 27, 2011

(54) METHOD OF REDUCING INFLOW OF WATER FROM A REACTOR OUTLET GAS TO A DEHYDRATION TOWER FOR SEPARATING CARBOXYLIC ACID SOLVENT AND WATER

(75) Inventor: Ki Joon Kang, Goyang-si (KR)

(73) Assignees: Ki Joon Kang, Gyeonggi-Do (KR);
Amtpacific Co., Ltd., Seoul (KR)

( * ) Notice: Subject to any disclaimer, the term of this patent is extended or adjusted under 35 U.S.C. 154(b) by 770 days.

(21) Appl. No.: 11/916,267

(22) PCT Filed: Feb. 15, 2007

(86) PCT No.: PCT/KR2007/000812
§ 371 (c)(1),
(2), (4) Date: Nov. 30, 2007

(87) PCT Pub. No.: WO2007/097543
PCT Pub. Date: Aug. 30, 2007

(65) Prior Publication Data
US 2009/0326264 A1  Dec. 31, 2009

(30) Foreign Application Priority Data

Feb. 20, 2006 (KR) .......................... 10-2006-0016331
Jan. 17, 2007 (KR) .......................... 10-2007-0005367

(51) Int. Cl.
*C07C 51/16* (2006.01)

(52) U.S. Cl. .......................... 562/414; 562/412; 562/409
(58) Field of Classification Search .......................... None
See application file for complete search history.

(56) References Cited

U.S. PATENT DOCUMENTS

| 6,143,925 A | * | 11/2000 | Tomitaka et al. ............. 562/412 |
| 6,153,790 A | | 11/2000 | June et al. |
| 2008/0097118 A1 | * | 4/2008 | Bartos et al. ................... 562/408 |

FOREIGN PATENT DOCUMENTS

| JP | 2003137833 | 5/2003 |
| WO | WO-96/11899 | 4/1996 |

* cited by examiner

*Primary Examiner* — Karl J Puttlitz
(74) *Attorney, Agent, or Firm* — Rabin & Berdo, P.C.

(57) ABSTRACT

A method of reducing or eliminating inflow of water to a dehydration tower using steam for separating water from a carboxylic acid from a reactor outlet gas produced in a reactor during oxidation of an aromatic compound in a carboxylic acid solvent to produce an aromatic acid, for example, oxidation of p-xylene in acetic acid solvent to produce terepthalic acid. The aromatic compound is introduced at the top of an absorption tower and collects ascending carboxylic acid solvent, introduced in the reactor outlet gas at the bottom of the absorption tower, for reintroduction into the reactor eliminating the need to remove and recover the solvent. The absorption tower, condensers and an organic-water separator remove the water in the reactor outlet gas as waste water, and the amount of water inflow to the dehydration tower is reduced or eliminated, as is the amount of steam required for separation.

11 Claims, 1 Drawing Sheet

[Fig. 1]
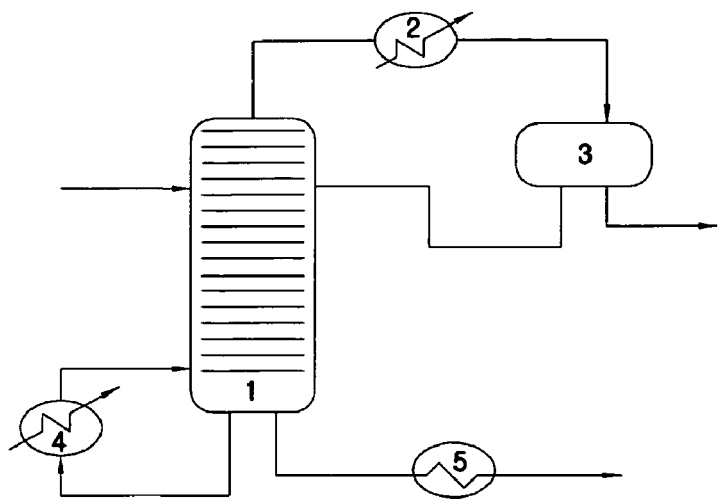
[Fig. 2]
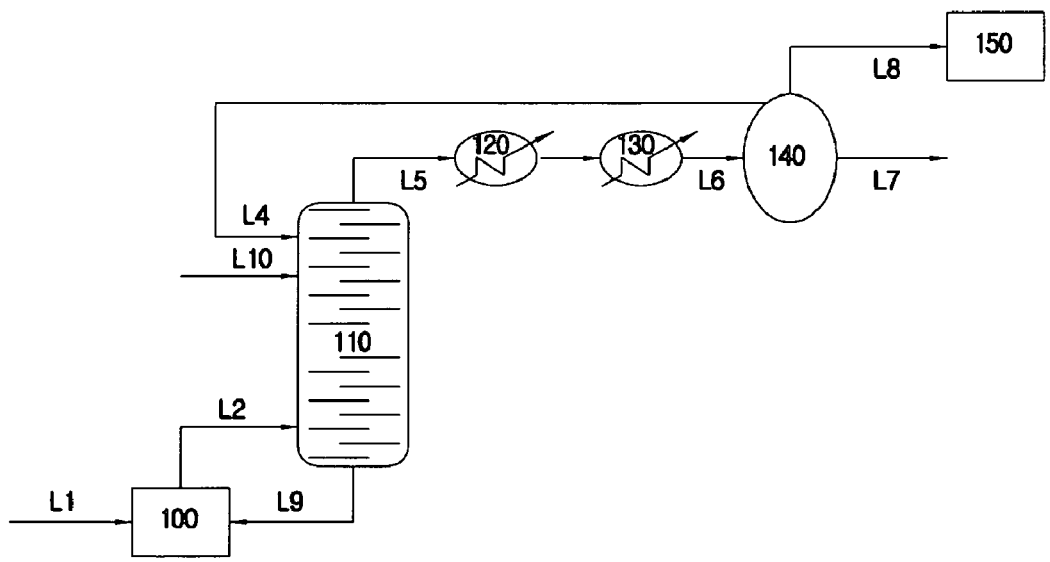

METHOD OF REDUCING INFLOW OF WATER FROM A REACTOR OUTLET GAS TO A DEHYDRATION TOWER FOR SEPARATING CARBOXYLIC ACID SOLVENT AND WATER

TECHNICAL FIELD

The present invention relates to a method for reducing water from a reactor outlet gas in the oxidation process of aromatic compounds by passing the reactor outlet gas through a first absorption tower and a condenser. As the amount of water inflow into the dehydration tower decreases, the amount of the steam required to separate water and acetic acid is reduced and the load of the dehydration tower can be reduced.

BACKGROUND ART

In general, the process of preparing terephthalic acid comprises an oxidation step of oxidizing p-xylene with air in the presence of a catalyst such as cobalt, manganese and bromide and a distillation step of recovering the acetic acid solvent from the reactor and removing water.

Typically, conventional distillation, azeotropic distillation, etc. are utilized to separate and collect acetic acid from water.

FIG. 1 illustrates the conventional process of collecting acetic acid through azeotropic distillation using an azeotropic agent.

Referring to the figure, the conventional apparatus for collecting acetic acid through azeotropic distillation using an azeotropic agent comprises a dehydration tower (1) for separating acetic acid from water through azeotropic distillation, a condenser (2) for condensing the outlet gas from the top of the dehydration tower (1), an organic-water separation tank (3) for separating the liquid organic materials passing through the condenser (2) from water, a heater (4) for supplying steam to the dehydration tower (1) and a heat exchanger (5) for cooling the acetic acid discharged at the bottom of the dehydration tower.

This conventional technology is advantageous in that, by adding an azeotropic agent to a mixture of water and acetic acid, the energy consumption by the dehydration tower (1) can be reduced since the resultant azeotrope boils at a temperature lower than the boiling point of water.

However, because the supply of steam is needed to collect acetic acid, additional energy is required to remove water.

The reactor outlet gas formed during the preparation of terephthalic acid is hot, 180° C. or higher, and includes non-compressible gases, e.g., nitrogen, acetic acid, p-xylene and water.

The reactor outlet gas is passed through several heat exchangers containing cooling water for heat exchange in order to gradually lower the temperature of the reactor outlet gas. Condensed acetic acid and some of water are returned to the reactor and the remaining water is sent to the dehydration tower for discharging.

The gas that has passed through the final heat exchanger includes a small amount of acetic acid and p-xylene. The gas is sent to a high-pressure absorption tower, where p-xylene is collected as entrained by acetic acid, acetic acid is collected as entrained by water and non-condensible gases including nitrogen are sent to a gas discharging unit and processed there.

The liquid mixture of acetic acid and water that has passed through the final heat exchanger and has been condensed is sent to the dehydration tower, where acetic acid is discharged at the bottom of the dehydration tower and water is discharged at the top of the dehydration tower.

DISCLOSURE OF INVENTION

Technical Problem

Although the method of separating acetic acid from water by gradually lowering the temperature of the reactor outlet gas using several heat exchangers is advantageous in that steam can be generated from the hot reactor outlet gas, energy consumption is inevitable since water has to be removed from acetic acid at the dehydration tower using steam.

Technical Solution

The present invention has been made to solve this problem and it is an object of the present invention to provide a method of reducing water from the reactor outlet gas in the oxidation process of aromatic compounds without further energy consumption.

To attain the object the present invention provides a method of reducing water from the reactor outlet gas in the oxidation process of an aromatic compound, which comprises: flowing the reactor outlet gas into the bottom inlet of a first absorption tower in which tray or packing is equipped as a means for increasing the gas-liquid contact surface; supplying an aromatic compound at the top inlet of the first absorption tower in order to collect the carboxylic acid selected from the group consisting of acetic acid, propionic acid and acrylic acid, and included in the reactor outlet gas, and to recover it through the bottom outlet of the first absorption tower; and discharging the water included in the reactor outlet gas along with the aromatic compound through the top outlet of the first absorption tower, condensing the water and the aromatic compound using a condenser, separating the water from the aromatic compound using an organic-water separator and discharging the water as wastewater.

The aromatic compound or the aromatic compound and part of the water separated by the organic-water separator are recycled to the first absorption tower and the gas discharged from the organic-water separator is transferred to a second absorption tower.

The aromatic compound is selected from the group consisting of o-xylene, m-xylene, p-xylene, benzene and toluene. Preferably, p-xylene is used.

ADVANTAGEOUS EFFECTS

First, since water is removed from the reactor outlet gas, the amount of the water removed at the dehydration tower is reduced and, also, the amount of steam used to separate water and acetic acid can be reduced.

Second, as the amount of the water removed at the dehydration tower is reduced, the load of the dehydration tower decreases, thereby increasing the capacity of the dehydration tower.

Third, since xylene compounds including p-xylene are used as aromatic compounds, the mixture discharged at the first absorption tower can be recycled to the reactor for the oxidation of the aromatic compounds, without using special separation apparatus.

BRIEF DESCRIPTION OF THE DRAWINGS

FIG. 1 illustrates the conventional process of collecting acetic acid through azeotropic distillation using an azeotropic agent.

FIG. 2 illustrates the process of reducing water from the reactor outlet gas in the oxidation process of terephthalic acid in accordance with an embodiment of the present invention.

BEST MODE FOR CARRYING OUT THE INVENTION

Hereunder is given a specific and detailed description of the method of reducing water from the reactor outlet gas in the oxidation process of aromatic compounds in accordance with the present invention, for a process of reducing water from the reactor outlet gas in the oxidation process of p-xylene for preparing terephthalic acid.

During the oxidation of p-xylene with air in the presence of a catalyst such as cobalt, manganese and bromide in the preparation process of terephthalic acid, acetic acid, which is used as solvent, and water, which is generated during the reaction, are discharged in the form of hot gas along with nitrogen and other gases. The inventor found out that, by removing water from the reactor outlet gas, it is possible to reduce the amount of water inflow into the dehydration tower and the amount of the steam required to separate water and acetic acid at the dehydration tower. Consequently, the load of the dehydration tower can be reduced or it becomes unnecessary to use the dehydration tower.

The liquid mixture of acetic acid, p-xylene and water that is discharged at the bottom outlet of the first absorption tower is recycled to the reactor for further production of terephthalic acid. Although variable depending on the extent of reaction, the liquid mixture comprises, in general, 10-60 wt % of acetic acid, 10-60 wt % of p-xylene and 3-40 wt % of water.

In general, terephthalic acid is prepared by air oxidation of p-xylene in the presence of a catalyst, as seen in the following Scheme 1. About 65 parts by weight of p-xylene is required to prepare 100 parts by weight of terephthalic acid.

Chemistry Figure 1

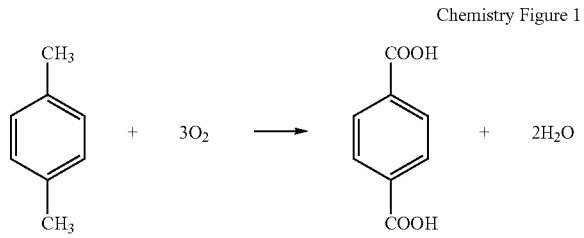

The water included in the reactor outlet gas is discharged at the top outlet of the first absorption tower along with excess p-xylene. The gas including p-xylene and water is condensed by the first heat exchanger into a stream of about 100° C., condensed by the second heat exchanger into a stream of about 40° C. and is transferred to the organic-water separation unit. p-Xylene is separated from water and collected there and water is discharged as wastewater. The gas discharged by the organic-water separator is a gas of about 40° C. or below and is transferred to the second absorption tower, which is a common high-pressure absorption tower, and processed there as in the conventional method.

The reactor outlet gas is flown into the first absorption tower directly or passing through several heat exchangers. For example, if the gas passes through 4 heat exchangers, the hot reactor outlet gas of 120-190° C. that has passed through the second and third heat exchangers is flown into the bottom inlet of the first absorption tower and water is removed from the reactor outlet gas as described above.

Preferably, the amount of the reactor outlet gas flown into the bottom inlet of the first absorption tower by splitting is determined depending on the amount of water to be removed in the entire preparation process of terephthalic acid.

The amount of water to be removed in the entire preparation process of terephthalic acid is 21-22 parts by weight per 100 parts by weight of the produced terephthalic acid and is calculated from 2 (moles of water)×18 (molecular weight of water)/166 (molecular weight of terephthalic acid)×100 (amount of terephthalic acid).

For example, if 500,000 tons of terephthalic acid is produced a year and the production amount per hour is 62.5 tons, the amount of required water per hour becomes 13.5 tons.

Provided that the air supplied for the reaction comprises 23% of oxygen and 77% of nitrogen and that all of the supplied air is oxidized, the amount of required oxygen is 3 (moles of oxygen)×32 (molecular weight of oxygen)/166 (molecular weight of terephthalic acid)×62.5 (production of terephthalic acid per hour)=36 tons and the amount of discharged nitrogen is 36×77/23=121 tons.

However, considering the oxidation efficiency of the reactor and the evaporation of liquid caused by the reaction heat, the amount of the total reactor outlet gas is determined between 300 and 700 tons.

And, preferably, the means for increasing the gas-liquid contact surface is constructed in the form of trays or packings.

The terms and words used in this specification and claims are not to be interpreted in common or literal meanings. Based on the principle that an inventor can adequately define the meaning of terms and words to best describe his/her own invention, they shall be interpreted in the meaning and context conforming to the spirit of the present invention.

Accordingly, the embodiment presented in this description and the accompanying drawing is only an example of the most preferred embodiment of the present invention. It will be appreciated by those skilled in the art that changes and modifications can be made without departing from the principles and spirit of the present invention, the scope of which is defined in the appended claims and their equivalents.

FIG. 2 illustrates the process of reducing water from the reactor outlet gas in the oxidation process of terephthalic acid in accordance with an embodiment of the present invention.

Referring to FIG. 2, the apparatus for removing water during the preparation of terephthalic acid in accordance with an embodiment of the present invention comprises a reactor (100), a first absorption tower (110), a first heat exchanger (120), a second heat exchanger (130), an organic-water separator (140) and a second absorption tower (150).

In an embodiment of the present invention, the first absorption tower (110) may be equipped with a means for increasing the gas-liquid contact surface, which may be constructed in the form of trays or packings, but the present invention is not limited thereby.

The first heat exchanger (120) cools the hot gas discharged at the top outlet of the first absorption tower (110). The first heat exchanger (120) may produce a low-temperature steam of about 100° C.

The second heat exchanger (130) condenses the gas that has passed through the first heat exchanger (120) and separates it into a liquid mixture of water and p-xylene and a nitrogen-containing gas.

Of the liquid mixture, p-xylene is separated by the organic-water separator and water is processed as wastewater through a pipe (L7). And, the gaseous material is transferred to the second absorption tower (150), a common high-pressure absorption tower, and processed there.

Hereinbelow, the process of removing water from the reactor outlet gas in the preparation process of terephthalic acid according to an embodiment of the present invention will be described in detail.

First, a reactor outlet gas discharged from a reactor (100) for the preparation of terephthalic acid is flown into the bottom inlet of a first absorption tower (110) via a pipe (L2) directly or passing through several heat exchangers.

The reactor outlet gas is cooled to 120° C. to 190° C. by a heat exchanger (not illustrated) before being flown into the first absorption tower (110). The reactor outlet gas comprises nitrogen, acetic acid, water and a small amount of organic materials. In general, the reactor outlet gas comprises 60-95 wt % of nitrogen, 1-18 wt % of acetic acid, 2-36 wt % of water and a small amount organic material, which may be methyl acetate, p-xylene, etc.

At the top inlet of the first absorption tower (110), the aromatic compound p-xylene is flown in via pipes (L4, L10). The amount of p-xylene is preferably 2-5 weight equivalents of the water to be removed. If the amount of p-xylene is outside this range, acetic acid may be discharged at the top of the absorption tower along with the gas, without being sufficiently collected or excess p-xylene may be discharged at the bottom of the absorption tower, thereby resulting in problems.

Of the pipes (L4, L10) through which p-xylene is flown into the top inlet of the first absorption tower (110), the pipe (L4) is the one through which a stream from the organic-water separator (140) to be described later is flown.

Next, the reactor outlet gas flown into the bottom inlet of the first absorption tower (110) rises to the top of the first absorption tower (110) and the p-xylene flown into the top inlet of the first absorption tower (110) descends to the bottom of the first absorption tower (110).

Inside the first absorption tower (110) is equipped a means for increasing the gas-liquid contact area constructed in the form of trays or packings. Passing through the trays or packings, the reactor outlet gas contacts p-xylene, during which process acetic acid and some of water included in the reactor outlet gas is absorbed by p-xylene and condensed to be collected at the bottom of the first absorption tower (110).

In this process, p-xylene acts as the solvent that absorbs the acetic acid and water included in the reactor outlet gas and, therefore, it is possible to recycle the liquid mixture discharged at the bottom of the first absorption tower (110) to the reactor (100) for the preparation of terephthalic acid via the pipe (L9), without the need of solvent removal.

And, if the amount of p-xylene included in the liquid mixture discharged at the bottom of the first absorption tower is larger than the amount of p-xylene required for the preparation of terephthalic acid, the p-xylene included in the liquid mixture may be separated by an organic-water separator to recycle it to the top inlet of the first absorption tower (110).

The water that has not been condensed at the bottom of the first absorption tower (110) is discharged to the top outlet of the first absorption tower (110) along with excess p-xylene and is condensed by condensers (120, 130), which may be heat exchangers. At the organic-water separator (140), p-xylene is separated from water and the water is processed as wastewater. In this process, the gas discharged by the organic-water separator (140), which comprises nitrogen, acetic acid and p-xylene, is transferred to the second absorption tower (150), a conventional high-pressure absorption tower, and processed there.

Subsequently, a mixture comprising 50-90 wt % of nitrogen, 5-30 wt % of p-xylene, 2-15 wt % of water, 5-500 ppm of acetic acid and a small amount of organic materials is discharged from the top outlet of the first absorption tower (110) via a pipe (L5). The mixture is cooled while passing through the first heat exchanger (120).

The temperature of the mixture flown into the first heat exchanger (120) is about 110° C. to 180° C. The temperature of the mixture that has been cooled while passing through the first heat exchanger (120) is about 100° C. At the first heat exchanger (120), a low pressure steam may be generated.

From the mixture that has been cooled while passing through the first heat exchanger (120), water and p-xylene included in the mixture are condensed as the mixture passes through the second heat exchanger (130).

Lastly, the mixture that has passed through the second heat exchanger (130) is separated by the organic-water separator (140).

In the organic-water separator (140), nitrogen, non-condensed p-xylene and a small amount of acetic acid are collected to the second absorption tower (150), which is a conventional high-pressure absorption tower, in gaseous state via a pipe (L8) and water is transferred to a wastewater processing system via a pipe (L7).

And, the p-xylene separated by the organic-water separator (140) is recycled to the top of the first absorption tower (110) via the pipe (L4).

Also, although not illustrated in the figure, some of water may be recycled to the first absorption tower (110) via another pipe in order to lower the concentration of the acetic acid that is discharged by the organic-water separator (140) along with water.

In accordance with the present invention, the amount of water to be removed at the dehydration tower is decreased because some of water is discharged at the top outlet of the first absorption tower (110). Therefore, the energy consumption by the dehydration tower is reduced.

Further, by carefully controlling the flow amount of the reactor outlet gas to the first absorption tower (110), the operation of the dehydration tower may be made unnecessary.

MODE FOR THE INVENTION

Practical and presently preferred embodiments of the present invention are illustrative as shown in the following example. However, it will be appreciated that those skilled in the art may, in consideration of this disclosure, make modifications and improvements within the spirit and scope of the present invention.

EXAMPLE

Inflow and outflow conditions at the first absorption tower are given in Table 1 below. The absorption tower had an inner diameter of 40 mm and the means for increasing the gas-liquid contact area was constructed in the form of random packing with a height of 1.5 m. In Table 1, PX stands for p-xylene and KGa for kg/cm$^2$ (absolute pressure).

TABLE 1

Inflow and outflow conditions at absorption tower

| Pipes | Composition (wt %) | Flow volume (g/hr) | Temperature (° C.) | Pressure (KGa) |
|---|---|---|---|---|
| L2 | Acetic acid (9.6)H$_2$O (19.3)N$_2$ (71.1) | 984 | 137 | 10.3 |
| L4 | PX (99.55)H$_2$O (0.45) | 228 | 35 | 10.3 |

TABLE 1-continued

Inflow and outflow conditions at absorption tower

| Pipes | Composition (wt %) | Flow volume (g/hr) | Temperature (° C.) | Pressure (KGa) |
|---|---|---|---|---|
| L10 | PX (99.99)$H_2O$ (0.01) | 234 | 35 | 10.3 |
| L9 | PX (52)Acetic acid (22)$H_2O$ (26) | 432 | 128 | 10.3 |
| L5 | PX (22)Acetic acid (25 ppm)$H_2O$ (12.5)$N_2$ (65.5) | 1072 | 123 | 10.3 |

As seen in Table 1, 189.9 g/hr of water ($H_2O$) was flown in via the pipe (L2) and 112.3 g/hr of water was discharged at the bottom of the first absorption tower (110) via the pipe (L9) and collected at the reactor (100).

Accordingly, the amount of water to be removed at the dehydration tower is reduced by 77.6 g/hr and the amount of steam to be used by the dehydration tower decreases. Thus, the energy consumption and load of the dehydration tower decrease.

INDUSTRIAL APPLICABILITY

As apparent from the above description, the method for reducing water from a reactor outlet gas in the oxidation process of aromatic compounds in accordance with the present invention decreases the amount of steam required to separate water and acetic acid at the dehydration tower and the load of the dehydration tower. Further, by carefully controlling the flow amount of the reactor outlet gas to the first absorption tower, the operation of the dehydration tower may be made unnecessary.

Those skilled in the art will appreciate that the concepts and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

The invention claimed is:

1. A method of reducing inflow of water from a reactor outlet gas to a dehydration tower that uses steam for separating carboxylic acid solvent and water, said water being produced in a reactor during oxidation of an aromatic compound in the carboxylic acid solvent to produce an aromatic acid, the method comprising the steps of:

flowing the reactor outlet gas that includes said carboxylic acid solvent and water into a bottom inlet of a first absorption tower equipped with means for increasing gas-liquid contact surface area, said carboxylic acid solvent being selected from the group consisting of acetic acid, propionic acid and acrylic acid;

supplying said aromatic compound at a top inlet of the first absorption tower to descend and collect therein the carboxylic acid solvent and a portion of the water from the reactor outlet gas as a mixture, condensing and removing the mixture as a condensate through a bottom outlet of the first absorption tower, and adding the condensate to the reactor; and discharging an additional portion of the water included in the reactor outlet gas and excess aromatic compound through a top outlet of the first absorption tower, condensing the water using a condenser, separating the water from the aromatic compound using an organic-water separator, and discharging the water from the organic-water separator as wastewater.

2. The method as set forth in claim 1, wherein the aromatic acid produced is terephthalic acid.

3. The method as set forth in claim 1, further comprising recycling the aromatic compound or the aromatic compound and a portion of water separated by the organic-water separator to a top inlet of the first absorption tower, and transferring gas discharged from the organic-water separator to a second absorption tower.

4. The method as set forth in claim 1, wherein the reactor outlet gas flown into the bottom inlet of the first absorption tower is a hot gas having a temperature ranging from 120 to 190° C., and is flown either (a) directly into the first absorption tower or (b) through several heat exchangers prior to being flown into the first absorption tower.

5. The method as set forth in claim 1, wherein the amount of the reactor outlet gas flown into the first absorption tower is controlled and corresponds to the amount of water to be removed.

6. The method as set forth in claim 1, wherein the means for increasing the gas-liquid contact surface area includes trays or packings.

7. The method as set forth in claim 1, wherein the aromatic compound is selected from the group consisting of o-xylene, m-xylene, p-xylene, benzene and toluene.

8. The method as set forth in claim 3, wherein the aromatic compound is selected from the group consisting of o-xylene, m-xylene, p-xylene, benzene and toluene.

9. The method as set forth in claim 4, wherein the aromatic compound is selected from the group consisting of o-xylene, m-xylene, p-xylene, benzene and toluene.

10. The method as set forth in claim 5, wherein the aromatic compound is selected from the group consisting of o-xylene, m-xylene, p-xylene, benzene and toluene, and is oxidized with air within the reactor to produce an aromatic acid that is terephthalic acid.

11. The method as set forth in claim 6, wherein the aromatic compound is selected from the group consisting of o-xylene, m-xylene, p-xylene, benzene and toluene.

* * * * *